US006322991B1

(12) United States Patent
Pearlman et al.

(10) Patent No.: US 6,322,991 B1
(45) Date of Patent: Nov. 27, 2001

(54) HIGH-THROUGHPUT SCREENS FOR ENZYME INHIBITORS

(75) Inventors: Ronald E. Pearlman; Leroi DeSouza, both of Toronto; J. Bryan McNeil, Newmarket; Evan M. McIntosh, Mississauga, all of (CA)

(73) Assignee: York University (CA)

( * ) Notice: Subject to any disclaimer, the term of this patent is extended or adjusted under 35 U.S.C. 154(b) by 0 days.

(21) Appl. No.: 09/136,920

(22) Filed: Aug. 20, 1998

Related U.S. Application Data
(60) Provisional application No. 60/056,508, filed on Aug. 21, 1997.

(51) Int. Cl.[7] ................................................. G01N 33/567
(52) U.S. Cl. ........................ 435/7.21; 435/5; 435/6; 435/253.1; 435/69.1; 435/69.8; 435/252.3
(58) Field of Search ................................ 435/7.21, 253.1, 435/69.1, 69.8, 71.1, 72.1, 252.3, 5, 6

(56) References Cited

U.S. PATENT DOCUMENTS 5,726,025 * 3/1998 Kirschner et al. ................... 435/7.2
5,753,235 * 5/1998 Haanes et al. ....................... 424/229.1
5,854,055 * 12/1998 Bloom et al. ........................ 435/253.1

OTHER PUBLICATIONS

McNeil, et al. "Yeast/herpes simplex virus TK gene fusions . . ." Current Genetics. 9:567–572, 1985.*
Holliday et al. "Inhibition of herpes simplex virus . . ." Antiviral Research. 16:197–203, 1991.*
"Yeast As A Model System To Study Drugs Effective Against Apicomplexan Proteins", A Companion To Methods In Enzymology 13, pp. 190–207.

* cited by examiner

Primary Examiner—Carla J. Myers
Assistant Examiner—Janell E. Taylor
(74) Attorney, Agent, or Firm—Katten Muchin Zavis

(57) ABSTRACT

The present invention provides a high-throughput screen for use in assaying for enzyme inhibitors of a target organism, comprising: a microorganism host in which an endogenous enzyme encoding gene has been replaced by a functionally complementing enzyme encoding gene from the target organism. The present invention also provides a method of identifying an inhibitor of a target organism enzyme, comprising the step of assaying a test inhibitor using a high-throughput screen comprising a microorganism host in which an endogenous enzyme encoding gene has been replaced by a functionally complementing enzyme encoding gene from the target organism.

25 Claims, 9 Drawing Sheets

FIGURE 5
FIGURE 6
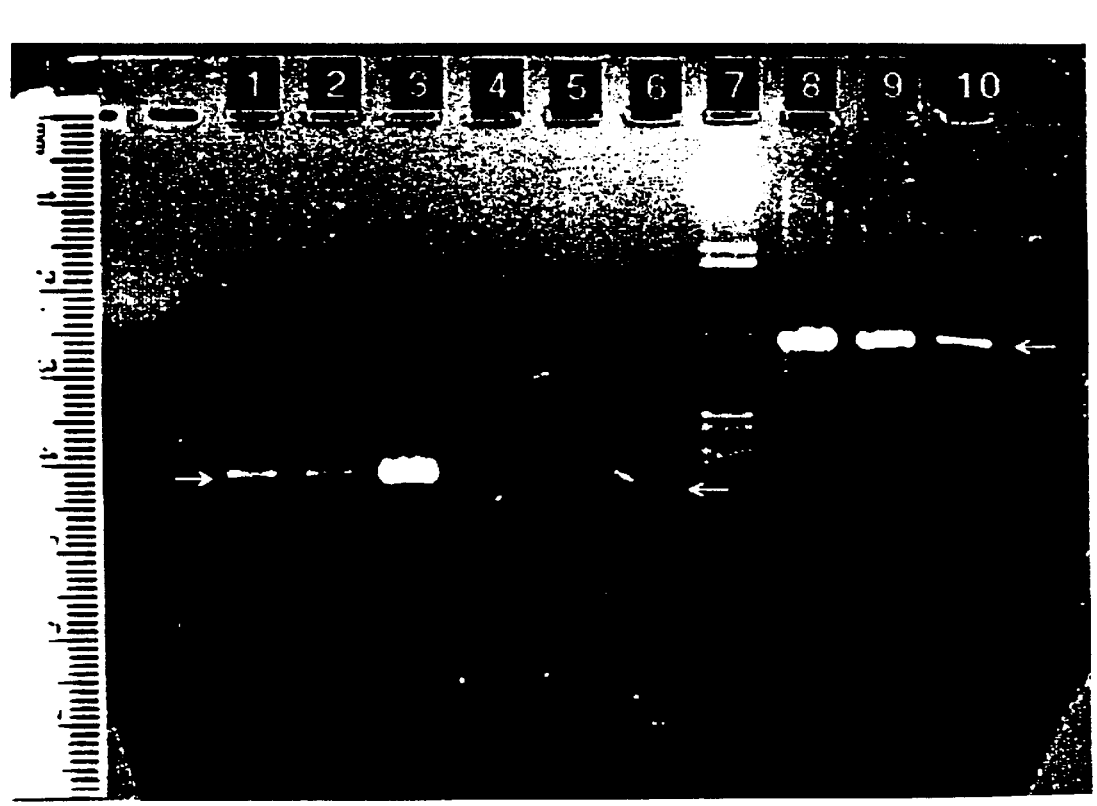

HIGH-THROUGHPUT SCREENS FOR ENZYME INHIBITORS

This application claims benefit of Ser. No. 60/056,508, filed Aug. 21, 1997.

FIELD OF THE INVENTION

The present invention related to the field of high-throughput screens. More specifically, the present invention relates to the field of high-throughput screens for enzyme inhibitors.

BACKGROUND OF THE INVENTION

Efficient and accurate replication of DNA and consequently, cell growth and survival, is dependent on the maintenance of a balanced nucleotide pool. The thymidylate synthesis pathway, shown in FIG. 1, plays a key role in maintaining this balance. The importance of the thymidylate synthesis pathway for cell survival has been recognized for a long time and this importance has often been exploited for chemotherapeutic purposes. The thymidylate synthesis pathway consists of two main branches; the de novo pathway and the salvage pathway. The de novo synthesis pathway leading to the conversion of deoxyuridine monophosphate (dUMP) to deoxythymidine monophosphate (dTMP) is present in all cells. Many organisms also utilize a salvage pathway for dTMP production whereby thymidine (TdR) is converted to dTMP through the action of the enzyme thymidine kinase (TK). Some fungi such as *Saccharomyces cerevisiae* lack a functional TK (Grivell and Jackson, 1968), and consequently do not possess this salvage pathway.

Two enzymes belonging to the thymidylate synthesis pathway that are of interest to researchers are deoxyuridine triphosphate pyrophosphatase (dUTPase), responsible for catalyzing the conversion of deoxyuridine triphosphate (dUTP) to deoxyuridine monophosphate (dUMP) and thymidylate synthetase (TS) responsible for the conversion of dUMP to deoxythymidine monophosphate (dTMP). dUTP is produced by the deamination of deoxycytosine triphosphate (dCTP) in some bacterial species, or through the conversion of dUMP to dUTP in most, if not all, organisms and some viruses. Hydrolysis of dUTP serves a dual function; it provides the cell with dUMP, the precursor for thymidylate synthesis, and also decreases the level of dUTP in the cell. The decrease in intracellular dUTP levels is of significance because DNA polymerase is capable of using dUTP as a substrate.

The enzyme dUTPase plays a key role in cell survival by providing the cell with deoxythymidine triphoshate(dTTP) and at the same time preventing misincorporation of uracil into DNA during replication. Studies which have shown dUTPase to be essential for the survival of organisms such as *Escherichia coli* and *S. cerevisiae*, provide supporting evidence for this stated importance. The discovery that dUTPase is encoded by viruses such as some of the pox viruses, retroviruses and herpes viruses, as well as the finding that decreased expression of the viral dUTPase is related to the reduced virulence of herpes simplex virus (HSV), have contributed substantially to suggestions of the importance of dUTPase as a potential target for the development of chemotherapeutic drugs.

Until recently the search for chemotherapeutic agents that affect the thymidylate synthesis pathway has focussed on targeting the enzyme TS which acts one step downstream from dUTPase (FIG. 1). TS requires 5,10-methylene tetrahydrofolate (5, 10-methylene THF) as a cofactor for catalyzing the conversion of dUMP to dTMP. 5,10-methylene THF is the methyl group donor used for the conversion of uracil to thymine. The focus on TS has resulted in the development of many drugs that target either TS directly or indirectly via the folate pathway. Some more commonly known drugs targeting TS include anticancer drugs such as 5-fluorouracil (FU) and 5-fluorodeoxyuridine (FdUrd) which inhibit TS directly (following metabolism to 5-fluorodeoxyuridylate), and methotrexate (also known as arnethopterin) and sulfanilamide, which act as inhibitors of the folate pathway. These folate pathway inhibitors inhibit the enzyme dihydrofolate reductase (DHFR) and the de novo synthesis of folates respectively, thus preventing the regeneration of 5,10-methylene THF. Another well known TS inhibitor, 5-fluorocytosine (FC) is used as an antifungal agent in the treatment of Candidiasis. The mechanism of action of FC is as follows; FC is first converted into FU by cytosine deaminase, which is metabolised to FdUrd and then to 5-fluorodeoxyuridine monophosphate (FdUMP) which inhibits TS. The inhibition occurs because FdUMP is an analogue of dUMP and can act as a competitive inhibitor of TS. Since the carbon-fluorine bond in FdUMP is much stronger than the carbon-hydrogen bond of the unsubstituted dUMP, TS is unable to catalyse its cleavage, leading to the competitive inhibition observed. Inhibition of TS results in a build up of dUMP and a corresponding decrease in dTMP, which in turn leads to increased dUTP within the cell and incorporation of uracil into DNA. The reiterative misincorporation and excision of uracil from DNA by the uracil repair mechanism, eventually leads to double strand breaks and the persistence of short "Okazaki-like" fragments and this eventually leads to cell death. The uracil excision repair mechanism is shown schematically in FIG. 2 and discussed in Tye and Lehman, (1977). Thus the cell death caused by inhibition of TS results from the altered ratio of dUTP to dTTP. Since this alteration in the dUTP/dTTP ratio can also be achieved by dUTPase inhibition, it is a potential target for the development of chemotherapeutic drugs.

It is possible that a dUTPase specific inhibitor could be used in the treatment of pathogenic infections as well as for cancer chemotherapy, in a manner similar to the TS inhibitors. Selective inhibition of a pathogen's dUTPase which leaves the host's dUTPase unaffected, should be an effective method of treatment, since that should result in the selective death of only the pathogen's cells. The fact that it is possible to find an inhibitor that would be specific for one organism's dUTPase and not another was demonstrated by various studies using 5-mercuri-2'-deoxyuridine (HgdUrd) and its thio derivatives, see, for example, Holliday and Williams, (1991).

One of the most time consuming and expensive steps in drug development is the finding "lead compounds" that can then be developed into drugs. The current approach to this problem is to generate libraries of compounds using combinatorial chemistry. Combinatorial chemistry generates these libraries by producing all possible combinations of a basic set of modular components. These 'modular components' are the characteristic groups defined as being necessary for a compound to interact with the target enzyme (or compound) (Hogan, 1996). Libraries generated by such combinatorial studies are then screened using a high-throughput screen (HTS) which assays the entire library for compounds that produce the desired effects. The four generally accepted requisites for an HTS, are as follows; a suitable compound library, an assay method configured for automation, a robotics workstation and a computer system for handling the data generated.

It is an object of the present invention to provide an in vivo system for use in assaying for enzyme inhibitors.

SUMMARY OF THE INVENTION

Accordingly, in one aspect the present invention provides a high-throughput screen for use in assaying for enzyme inhibitors of a target organism, comprising: a microorganism host in which an endogenous enzyme encoding gene has been replaced by a functionally complementing enzyme encoding gene from the target organism.

In another aspect, the present invention provides a high-throughput screen for use in assaying for dUTPase inhibitors of *Candida albicans*, comprising: *S. cerevisiae* in which endogenous dUTPase has been replaced with dUTPase encoding gene from *C. albicans*.

In another aspect, the present invention provides a high-through put screen for use in assaying for dUTPase inhibitors of human cells, comprising: *S. cerevisiae* in which endogenous dUTPase has been replaced with dUTPase encoding gene from human cells.

In yet other aspects, the present invention provides: *S. cerevisiae* in which endogenous dUTPase has been replaced with dUTPase encoding gene from *C. albicans*, deposited at ATCC under accession no. 74421; *S. cerevisiae* in which endogenous dUTPase has been replaced with dUTPase encoding gene from *C. albicans* and which further comprises a cloned thymidine kinase encoding gene from Herpes Simplex Virus, deposited at ATCC under accession no. 74423; *S. cerevisiae* in which endogenous dUTPase has been replaced with dUTPase encoding gene from human cells, deposited at ATCC under accession no. 74420; and *S. cerevisiae* in which endogenous dUTPase has been replaced with dUTPase encoding gene from human cells and which further comprises a cloned thymidine kinase encoding gene from Herpes Simplex Virus, deposited at ATCC under accession no. 74422. The above cultures, ATCC accession numbers 74420, 74421, 74422, and 74423, were deposited under the Budapest Treaty with the American Type Culture Collection (ATCC), 12301 Parklawn Drive, Rockville, Md. 20852 on Jun. 27, 1997.

Further, the present invention also provides a method of identifying an inhibitor of a target organism enzyme, comprising the step of assaying a test inhibitor using a high-throughput screen comprising a microorganism host in which an endogenous enzyme encoding gene has been replaced by a functionally complementing enzyme encoding gene from the target organism.

BRIEF DESCRIPTION OF THE FIGURES

Preferred embodiments of the present invention will be described, by way of example only, with reference to the attached Figures, as identified below:

FIG. 5: Southern blot analysis of *S. cerevisiae* strains constructed;

FIG. 6: PCR analysis of *S. cerevisiae* strains constructed;

DESCRIPTION OF THE PREFERRED EMBODIMENTS

Figure 1:
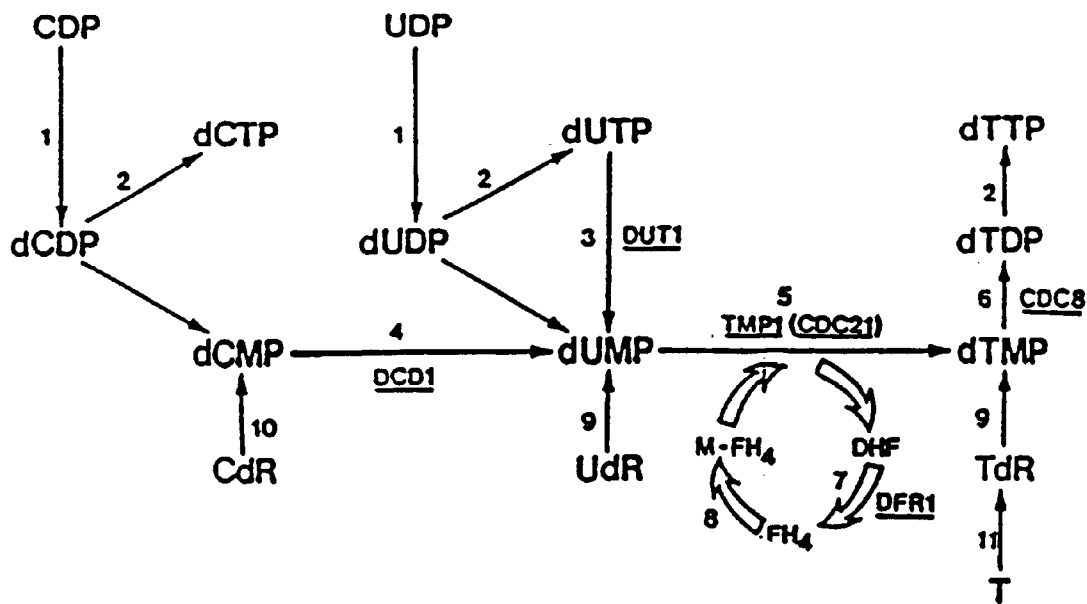
FIG. 1: The thymidylate synthesis pathway.

A high-throughput screen in accordance with the present invention generally comprises a microorganism host containing a functionally complementing cloned enzyme encoding gene from a selected target organism, such as a human cell, a virus, a fungus or a pathogenic organism.

In the presently preferred embodiment, the microorganism host is a yeast host such as *S. cerevisiae*. *S. cerevisiae* is a well characterized eukaryote with a short generation time, permitting one to obtain screening results relatively quickly. In addition, the knowledge of its entire genomic sequence and the ready availability of vectors and strains makes genetic and molecular manipulation in *S. cerevisiae* relatively simple. Furthermore, haploid strains of *S. cerevisiae* are available, thus necessitating the manipulation of only a single copy of the gene . Lastly, as will be described in more detail below, the inhibition of dUTPase in *S. cerevisiae* results in the display of a characteristic dumbbell shaped morphology. Scoring for inhibited cells is therefore a relatively quick, inexpensive and convenient method of verifying the results of growth rate assays, that is suggestive of the ability of a particular drug to inhibit dUTPase.

The cell cycle in *S. cerevisiae* is similar to that in other eukaryotes with four stages ($G_1$, S, $G_2$, and M). A host of enzymes such as the Cell Division Cycle (CDC) proteins control the transition through the various stages. Temperature sensitive CDC mutants, as well as various inhibitory compounds that are specific for different stages in the cell cycle have often been used in the characterization of the features of the various cell cycle stages. An example of an inhibitory compound that is stage specific is the microtubule inhibitor nocodazole which arrests the cell cycle before mitosis. Examples of CDC genes that have been studied for their effects on the cell cycle are, CDC6p which controls the transition into the early S phase, CDC28 (the *S. cerevisiae* homologue of CDC2) which controls the transition into S phase and then again into the M phase of the cycle and CDC35 which acts at the $G_1$ phase. Mutants in these genes arrest at the specific stage in the cell cycle at which these gene products act making it easy to identify the morphology of the various stages. Thus CDC28 mutants arrest as large unbudded cells which corresponds to the late $G_1$ phase, CDC 35 mutants arrest as small unbudded cells corresponding to early $G_1$, CDC 4 and CDC7 mutants arrest as budded cells corresponding to the early S phase and CDC17 mutants arrest as cells with larger buds corresponding to late S phase. Thus *S. cerevisiae* cells in S phase display small to large buds indicative of early to late stages and cells in late S phase display "FIG. 8" or "dumbbell" shapes as a result of the mother and budding daughter cells being of roughly equal size. Cells lacking any buds are in the $G_1$ phase of the cycle. Since DNA replication occurs during S phase, disruption of any of the processes that influence DNA replication affects the S phase. The inhibition of DNA replication therefore results in the persistence of the easily distinguishable dumbbell shaped morphology (McIntosh et al., 1986). Like the other enzymes involved in the thymidylate synthesis pathway, dUTPase plays a key role in allowing DNA replication to proceed smoothly, therefore its inhibition would affect the cell at the S phase. *S. cerevisiae* defective in dUTPase exhibit growth arrest with the classic dumbbell phenotype.

The design of a *S. cerevisiae* based high-throughput screen for testing potential enzyme inhibitors, such as dUTPase inhibitors, requires the construction of haploid strains of *S. cerevisiae* in which the endogenous enzyme encoding gene (e.g., DUT1) is replaced with the enzyme encoding gene (DUT) of another organism. An inherent property of the system is the ability of the exogenous enzymes to be capable of functional complementation in *S. cerevisiae*. As will be discussed below, DUT genes from *C. albicans*, herpes simplex virus (HSV) and human cells have been successfully introduced into *S. cerevisiae*. A compound which causes the inhibition of growth of one of the *S. cerevisiae* strains with the *C. albicans* or HSV DUT and not the stains with human DUT would be a likely candidate for a *C. albicans* specific or HSV specific dUTPase inhibitor. The likelihood of such a compound being specific for the *C. albicans* or HSV dUTPase is high since the difference in inhibition between the strains can only be explained on the basis of their different dUTPases.

In a preferred embodiment of the present invention, the microorganism host if further modified by the incorporation of a GAL1 upstream activator sequence (UAS) element 5' to the exogenous DUT gene. This allows for inducible expression of the gene.

This GAL1 promoter allows for high level inducible expression of the exogenous dUTPase.

In a high-throughput screen comprising a microorganism host containing exogenous dUTPase encoding gene and GAL1 promoter, compounds which specifically inhibit the target dUTPase will exhibit a DNA synthesis-arrest cell morphology when grown in, for example, glucose but will exhibit a dosage-dependent resistance to the compounds when over expression of the target dUTPase in induced by growth in galactose.

The galactose dependence provides evidence of specificity, i.e., that the compounds are inducing toxicity through inhibition of the dUTPase in particular and not through other enzymes essential to DNA replication. As will be apparent, there are other inducible promoters which could be utilized.

A high-throughput screen in which endogenous dUTPase encoding gene has been replaced with human dUTPase encoding gene is useful in identifying potential antifungal and antiviral compounds, i.e. it is useful in determining whether a compound which inhibits *C. albicans* or HSV dUTPase also inhibits human dUTPase. As will be apparent, to be a safe, useful antifungal or antiviral pharmaceutical, a compound must not adversely effect human dUTPase activity.

dUTPases are specific for dUTP. Accordingly, the most likely inhibitors of dUTPase are expected to be deoxyuridine analogues. Two structurally characterized dUTPases, namely *E. coli* and human, possess the capacity to interact with the phosphate group of a nucleotide substrate. This raises the possibility that inhibitors may be required to be in nucleotidic form. Unfortunately, *S. cerevisiae* is not well adapted to nucleotide uptake so nucleosidic test compounds will likely be preferred. As *S. cerevisiae* lacks an endogenous thymidine kinase (TK), it is a preferred aspect of the present invention to introduce an exogenous TK which is capable of functioning in *S. cerevisiae*. The introduction of an exogenous TK gives the *S. cerevisiae* the ability to take up nucleosidic test compounds and convert them internally to their nucleotidic form.

The selection of a microorganism host is not limited to the specific yeast *S. cerevisiae* discussed above. Other suitable microorganism hosts include other yeasts such as *Schizosaccharomzyces pombe*, non-yeast fungi, bacteria and eukaryotes. One of the criteria in determining a suitable microorganism host is to identify a host in which replication inhibition is readily determined. Replication inhibition need not necessarily be determined by looking for cells having a dumb-bell shaped morphology. It is envisioned, for example, that replication inhibition in a bacterial host may be followed by measuring the optical density of the cell culture.

As will be apparent, different microorganism hosts will have different abilities to uptake nucleosidic and/or nucleotidic test compounds and some microorganism hosts will have endogenous thymidine kinase. Accordingly, it will not always be preferable to introduce an exogenous thymidine kinase. The determination of whether or not to introduce an exogenous thymidine kinase is believed to be within the purview of a person of skill in the art.

The selection of a suitable enzyme encoding gene for insertion into the microorganism host is not particularly limited. It is envisioned that a high-throughput screen in accordance with the present application may be adapted to assay for inhibitors of any of the so-called "essential enzymes" in the nucleotide metabolism and DNA replication pathways. Examples of such "essential enzymes" include the dUTPase discussed above, DNA ligase, thymidylate synthase, thymidylate kinase, serine hydroxymethyl transferase and dihydrofolate reductase.

Further, the type of target organism is not limited and may be, for example, a virus such as Herpes Simplex Virus (HSV), a fungus such as *Candida albicans*, a bacteria or any eucaryotic pathogen such as protozoa. Specific examples of potential target organisms include *Plasmodium falciparum* (malaria) and *Aspergillus fumigatus*.

In a presently preferred embodiment of the invention, a high-throughput screen for use in assaying for inhibitors of *C. albicans* comprises a host microorganism *S. cerevisiae* in which the endogenous dUTPase encoding gene is replaced with the dUTPase encoding gene from *C. albicans*.

*C. albicans* is normally a harmless microbe found in the oral cavity and the digestive and uro-genital tracts of humans. It is, however, opportunistic in nature and can cause serious complications in individuals whose immune systems have been compromised such as following invasive surgery, or in the case of AIDS or cancer patients. With these categories of individuals on the rise in recent years, Candidiasis is rapidly becoming a cause for concern. One of the reasons for this concern is the limited number of safe and effective treatments for Candida infections. One of the common treatments involves the use of 5-fluorocytosine (FC) described earlier. The basis of its action as stated before is the conversion of FC to FU by cytosine deaminase. Since mammalian cells do not encode a cytosine deaminase, they are unaffected by FC. A major drawback of FC is that, strains of *C. albicans* readily emerge that are resistant to FC, making the search for other effective anti-Candida agents more urgent. The fact that the response of *C. albicans* dUTPase to potential dUTPase inhibitors namely HgdUrd has been studied, combined with the ability of the *C. albicans* dUTPase to functionally complement in *S. cerevisiae*, which is the preferred host for the dUTPase inhibitor screen system of the present invention, makes it a good target organism.

In alternative embodiments of the present invention, the endogenous dUTPase encoding gene of *S. cerevisiae* is replaced with the dUTPase encoding genes from herpes simplex virus (HSV) and human cells.

Studies on HSV dUTPase in vitro as well as in human cells have demonstrated that inhibition of HSV dUTPase could result in a decrease in viral replication. This makes HSV dUTPase inhibition a plausible course of action for the development of anti-viral drugs. Since HSV dUTPase is very different from eukaryotic trimeric forms, successful adaptation of the screen system of the present invention to include the search for inhibitors specific for HSV dUTPase has proved the universality of the high-throughput screen of the present invention.

Full details on the preparation, isolation, characterization and testing of three haploid strains of S. cerevisiae, in which the endogenous dUTPase encoding gene has been successfully replaced by the dUTPase encoding gene from HSV, C. albicans and human cells, respectively, is provided in the following Example.

The legends for FIGS. 1–8 may be found in Appendix A. The full citations for all references referred to in the present specification may be found in Appendix B and the Tables referred to may be found in Appendix C.

EXAMPLE

Materials and Methods

Strains, plasmids, primers and media used or made are as listed in Tables 1, 2, 3, and 4 respectively. Buffers and other solutions used routinely are listed in Table 5. Media for growth of E. coli were prepared as described in Sambrook et al. (1989). With the exception of MSA media and FOA plates, media for the growth of S. cerevisiae were prepared as described in Sherman (1991). MSA medium was prepared as specified in Little and Haynes (1979), while the FOA plates are described in Sikorski and Boeke (1991). All media preparations were steam and pressure autoclaved for 20 minutes. Primers used were synthesized by Dalton Chemicals, Toronto. The potential dUTPase inhibitors tested were supplied by Oncorpharm Ltd., Gaithersburg, Md., U.S.A. HgdUrd was synthesized according to the protocol of Bergstrom and Ruth (1977).

Conditions for Growth

E. coli host strains were grown at 37° C. in YT, while those carying plasmids were grown in YT+ampicillin. The vector encoded ampicillin resistance (β-lactamase gene) was used in the selection and maintenance of transformants. Ampicillin in the media was at a final concentration of 50 μg/ml.

S. cerevisiae were grown at 30° C. Cultures were usually grown in 5 ml volumes in 18×150 mm test tubes with vigorous shaking. When required, SD medium was supplemented with adenine, methionine, histidine, tryptophan, uracil, and leucine at a final concentration of 50 μg/ml each. Selection of transformants in the case of S. cerevisiae was for the appropriate prototrophy conferred by the plasmid vectors, usually leucine or uracil.

DNA Manipulations

Plasmid DNA used for subcloning and restriction mapping was isolated from E. coli by the alkaline lysis mini-prep method (Sambrook et al., 1989). When necessary, purification of this plasmid DNA was achieved by phenol-chloroform extraction (Sambrook et al., 1989). Digestion of plasmid DNA was carried out at 37° C. for two or three hours with a 2–10 fold excess of restriction enzymes. DNA fragments after restriction digestion were resolved by electrophoresis through 0.8% or 1.5% agarose gels. When required, fragments of interest were purified from agarose gels by centrifugation of the appropriate gel slices through glass wool (Heery et al, 1990). Ligations were performed as described in Sambrook et al. (1989). Ligation products were transformed into E. coli DH5αF'. On isolation and restriction mapping of the plasmids, those containing an insert of interest were transformed into S. cerevisiae. All restriction enzymes, T4 DNA ligase and enzyme buffers were from New England Biolabs.

Isolation of S. cerevisiae Genomic DNA

S. cerevisiae genomic DNA was isolated using a modification of the procedure described by Sikorski and Boeke (1991). 5 ml of fresh overnight culture was centrifuged in 13×100 mm test tubes, in a Sorvall centrifuge for 5 minutes at 3000 rpm in a SA600 rotor. After removing the supernatant, 400 μl of TE was added to the pellet. Acid washed glass beads (0.45 mm, Sigma) were added to just below the meniscus and the tubes vortexed until 90% of the cells were lysed, as determined by phase-contrast microscopy. 40 μl of 10% SDS was added to the tube which was then incubated at 65° C. for 5 minutes. The cell suspension was transferred into an Eppendorf tube and centrifuged for 5 minutes at 12,000×g. The supernatant was transferred to a clean tube, to which 150 μl of Solution III from the alkaline mini-prep method (Sambrook et al., 1989) was added. The procedure following this step was the same as the alkaline-lysis method for the isolation of plasmid DNA. Following ethanol precipitation and phenolchloroform extraction the pellet was resuspended in 100 μl of TE.

Isolation of total RNA from S. cerevisiae.

The method described by Kohrer and Domdey (1991) for the isolation of S. cerevisiae total RNA was scaled down and modified for convenience. Briefly, 5 ml of culture at an $OD_{600}$ of 5–10 was centrifuged at 2500 rpm in a Sorvall SA600 rotor for 5 minutes. The supernatant was removed and the cells resuspended in 0.5 ml sodium acetate buffer (Table 5). This was transferred into Eppendorf tubes to which 50 μl of 10% SDS and 0.6 ml phenol (prewarmed to 65° C.) was added. The tubes were alternately vortexed for 30 seconds and heated in a 65° C. water bath for 30 seconds for a total of five minutes, after which they were cooled quickly on ice to room temperature. They were then centrifuged and the organic phase removed. This extraction with phenol was repeated following which the aqueous phase was collected in a fresh tube. An equal volume of chloropane was added and the tube vortexed for 2 minutes. The aqueous phase was once again separated by centrifugation, transferred to a fresh tube and extracted with an equal volume of chloroform-isoamyl alcohol (24:1). The aqueous phase was isolated and precipitated with 2 volumes of 95% ethanol and 1/10 volume of 3M sodium acetate (pH 5.3). Finally the RNA was pelleted, washed with 70% ethanol and resuspended in sterile $dH_2O$.

PCR Amplifications

PCR amplifications were carried out using a Perkin Elmer 9600 thermal cycler. In a 50 μl PCR reaction, 25 pmoles of primers (forward and reverse) and 0.25 μg–0.5 μg of template DNA were used. The concentrations of dNTP mix and $MgCl_2$ were 0.25 mM of each nucleotide and 1.5 mM respectively. Taq or Tsg polymerase used was from Sangon, Toronto. PCR programs used included cycles of 94° C. for 30 seconds, 43° C. or 55° C. for 30 seconds (primer dependent; see Results) and 72° C. for 2 minutes. The number of cycles used was template dependent. In the case of plasmid DNA and DNA fragments 25 cycles were used, while in the case of genomic DNA this number was raised to 30. A final extension at 72° C. for 7 minutes was also employed. When necessary, purification of the PCR products was done as described in the DNA manipulation section.

Transformation of Cells

E. coli were transformed by electroporation using the BRL cell porator and voltage booster. Electro-competent cells were prepared by growing the cells in 1 litre of YT to an $OD_{600}$ of 0.5 to 1.0. Cells were harvested after chilling on ice for 15–30 minutes and pelleted by centrifugation at 4000×g for 15 minutes in a cold rotor. The pellet was washed three times, once in 1 L of cold, sterile $dH_2O$, a second time in 500 ml of $dH_2O$, and a third time in 20 ml 10% glycerol. The final pellet was resuspended in 2–3 ml 10% glycerol, quick frozen in 100 μl aliquots in dry ice/ethanol and stored at −70° C. 20 μl cells and 1 μl DNA (0.1–0.5 μg) were mixed as recommended by the manufacturer's protocol, and a pulse of 2.45 KV was applied to the cells. Settings on the cell porator were; 330 μF (capacitance), low Ω (DC volts) and fast charge rate. The voltage booster was set at 4 KΩ. After electroporation, the cells were transferred to 2 ml SOC medium, incubated at 37° C. for 45 minutes with shaking and spread on the appropriate selective plates.

Transformation of S. cereviasiae cells was by the one-step transformation procedure described by Chen et al., (1992).

Southern Hybridization

S. cerevisiae genomic DNA was digested with restriction enzymes and electrophoresed through a 1% agarose gel. After denaturation and neutralization, the DNA was transferred onto a Gene Screen Plus nylon membrane (Dupont NEN ) as described in Sambrook et aL, (1989). After the transfer was completed, membranes were placed in 6× SSPE for 5 minutes, put in 0.4N NaOH for about 3 minutes, neutralized in 2× SSPE with 0.2N Tris HCI (pH 7.4) for 5 minutes and air dried. Prehybridization was done in a shaking water bath at 65° C. for approximately two hours. The prehybridization mix contained 5× SSPE, 1.0% SDS, and 0.5% (w/v) fat free skimmed milk powder. Probes were made by the random priming method (Fienberg and Vogelstein, 1983). Unincorporated label was removed by passage through a Sephadex G25 spun column. The probe was added to the prehybridization solution to approximately $10^6$ cpm/ml. Hybridization was carried out in a shaking water bath at 65° C. for 16–20 hours. Following hybridization, the filters were washed for 10–15 minutes in 2× SSPE with 0.1% SDS at 50° C. A second wash in 1× SSPE with 0.1% SDS for 10 minutes, and a final wash in 0.5× SSPE with 0. 1% SDS for the same length of time, were done at room temperature. The filters were then wrapped in Saran wrap and either imaged with a Canberra Packard Instantimager or exposed to Kodak XAR 5 X-ray film with Quanta III intensifying screens for 1–2 days at −70° C.

Northern Hybridization

The procedure followed for Northern Hybridizations was similar to that used for the Southern analysis. The gel apparatus and solutions used were made RNase free using procedures described in Sambrook et al. (1989). The RNA was separated on an 1.0% agarose gel and transferred to Gene Screen Plus filters as described previously except that the NaOH treatment was omitted. Filters were prehybridized and hybridized at 65° C. as described for the Southern hybridizations. The PstI-EcoRI fragment from p22.22, Candida DUT or Human DUT coding sequences were used as probes.

Results

I. Construction and characterization of S. cerevisiae strains for the expression of heterologous DUT genes.

The replacement of the endogenous S. cerevisiae DUT-gene by the human DUT and HSV DUT, was achieved using the same approach as that used for the creation of the C. albicans DUT containing strain (DeSouza, 1995). A schematic representation of this approach is presented in FIG. 3.

HSV DUT was PCR amplified using the HSX and HSB primers (Table 3), and the Hpal-BglII fragment from HELIR1RV plasmid (Table 2) as the template. Conditions for PCR amplification were as described in Materials and Methods. The annealing temperature used was 43° C. The PCR amplified HSV DUT gene was ethanol precipitated, resuspended in distilled water, and digested with XbaI and BglII. Digestion products were purified by gel electrophoresis and extracted from the gel using the method of Heery et al. (1990). The HSV DUT gene was cloned into the XbaI-BamHI sites of pLD7. The resulting construct called pLD3, contained the HSV DUTcoding region flanked by the S. cerevisiae DUT flanking regions with the GAL1 UAS element approximately 200 bp 5' to the translation start site (FIG. 4). This construction was confirmed using restriction mapping. The plasmid linearized with BglII, was used to transform the S. cerevisiae K2300 strain (Table 1). Since pLD 3 contained a URA3 marker, the transfonnants were selected on the basis of uracil prototrophy. These transformants now contained the HSV DUT gene in tandem with the endogenous DUT gene. The site specific insertion of the HSV DUT gene occurred by the targeted homologous recombination resulting from transformation with the linearized plasmid. Two colonies designated HS4.1 and HS4.2 were confirmed by PCR analysis, using genomic DNA as template and HSX and HSB primers, to contain the HSV DUT. PCR conditions were the same as those used earlier for the amplification of the HSV DUT gene from the HELIR1RV fragment with the exception of the annealing temperature which in this case was 55° C. HS4.1 and HS4.2 were transformed with p1313 (Table 2), which is a plasmid that contains the S. cerevisiae DUT gene. H4.2 and H4.3 (Table 1) were also transformed with p1313. These were two previously constructed S. cerevisiae strains which, in a fashion similar to HS4.1 and HS4.2, contained the human DUT and the endogenous DUT in tandem. These transformants were selected on the basis of their leucine prototrophy. Colonies prototrophic for leucine were picked and grown in 5 ml of defined media (SD supplemented with methionine, uracil, adenine, tryptophan and histidine) to saturation, reinoculated into fresh tubes and once again grown to saturation. An aliquot (10 μl in the case of H4.2 and H4.3, and 100 μl in the case of HS4.1) of these saturated cultures were then plated on FOA plates, which select for uracil auxotrophy. These uracil auxotrophs can result from one of two possible intramolecular homologous recombination events (FIG. 3) or from a mutation in the URA3 gene. The recombination events result in the excision of the URA3 gene along with one of the two DUT genes. Excision of the endogenous DUT results in the retention of the exogenous DUT and thus in the effective replacement of the S. cerevisiae DUT by the human or HSV equivalent.

A Southern blot analysis was used to screen colonies growing on the FOA plates. Twelve colonies from the HS4.1 containing FOA plate and six colonies from each of the H4.2 and H4.3 containing FOA plates were picked, grown in YEPD and the genomic DNA isolated. This DNA was digested with BamHI, electrophoresed through a 1.0% agarose gel, and transferred to Gene Screen Plus membrane as described in Materials and Methods. The membranes were hybridized using the PstI-EcoRI fragment from p22.22 (Table 2) as a probe. Colonies in which the endogenous DUT had been replaced by the exogenous DUT have a unique fragment of approximately 1.0 Kb, caused by the presence of the BamHI site on the 3' end of the exogenous DUT gene (FIG. 3A). In the case of the human DUT, this site had previously been introduced in the 3' primer used for the PCR amplification of the human DUT and had subsequently been used to subclone the gene into the XbaI-BamHI sites of pLD7 in the same way as was done for the construction of pLD3. In the case of the HSV DUT, there was no BamHI site in the 3' primer used for PCR amplification, however, there is a BamHI site in the coding sequence approximately 180 bp from the 3' end of the gene which results in the corresponding fragment being approximately 1.2 Kb in length. Since no BamHI site is present in a similar location in the endogenous gene (FIG. 3B), the presence of this fragment can be considered diagnostic of the replacement of the endogenous DUT by an exogenous DUT.

Of all colonies screened in this manner, two colonies in which the human DUT and three colonies in which the HSV DUThad replaced the endogenous DUTwere found. These were designated H4.31 and H4.32 in the case of the strains with the human DUT and HS4.13, HS4.16 and HS4.111 in the case of the HSV DUT containing strains. These clones were subsequently cured of p1313 by growth for 20–30 generations in non selective (YEPD) media. Screening for colonies cured of p1313 was done by replica plating onto defined media plates, with and without leucine. Colonies lacking the plasmid were inoculated into YEPD, cultures grown and genomic DNA isolated. A Southern analysis was repeated to confirm the construction, along with genomic DNA from K2300 as a negative control and genomic DNA from C4.32 (S. cerevisiae strain containing the C. albicans DUT gene; Table 1) as a positive control. FIG. 5 lanes 2, 3, 4 and 5 shows the results of the Southern analysis on K2300, C4.32, H4.31 and HS4.13 respectively. The 1.0 Kb fragment present in the C4.32 and H4.31 lanes is not present in the K2300 lane and is slightly larger (approximately 1.2 Kb) in the HS4.13 lane.

As a further confirmation of the strain construction, PCR amplification was performed using the genomic DNA isolated from one clone of each of the Candida DUT, human DUT and HSV DUT containing strains. The primers used in each case were specific to the DUT gene which replaced the S. cerevisiae gene. Thus in the case of the Candida DUT containing strain the primers were CDUTHIS and CDUT, in the case of the human DUT containing strain they were HUX and HUB and in the case of the HSV DUT containing strain they were HSX and HSB (Table 3). In all these cases the annealing temperature used was 55° C. and the number of cycles was 30. FIG. 6, lanes 1, 4 and 8 show the PCR products after electrophoresing through a 1.5% agarose gel. The differences in the sizes of these fragments appropriately reflect the differences in the sizes of the coding sequences of the three genes in question. Thus the PCR product resulting from the reaction mix with C4.32 genomic DNA was a fragment of approximately 0.47 Kb which is the size of the C. albicans DUT coding sequence (FIG. 6, lane 1). PCR reaction mixes with H4.31 and HS4.13 genomic DNA produced 0.45 Kb and 1.1 Kb fragments which are the sizes of the human and HSV DUT coding sequences respectively (FIG. 6, lanes 4 and 8).

A Northern blot analysis on K2300, C4.32 and H4.3, as well as a later slot blot analysis using total RNA isolated from all four strains (i.e. K2300, C4.32, H4.31 and HS4.13), provided the final confirmation for the construction of the strains. Induction of transcripts in the presence of galactose was also demonstrated.

Introduction of a thymidine kinase (TK) gene into the S. cerevisiae strains

The HSV thymidine kinase (HSV TK) present on the plasmid pJM81 (Table 2) was introduced into the S. cerevisiae strains. This plasmid contains the entire His3 gene along with the promoter and the first 142 codons of an uncharacterized gene fused to the HSV TK. The reading frame of the uncharacterized gene is the same as that required for the expression of the TK resulting in the generation of a fusion protein which possesses thymidine kinase activity (McNeil and Friesen, 1981; McNeil and Little, 1985). pJM81 was transformed into K2300, C4.32, H4.31 and HS4.13 by the one-step transformation method (Chen et al., 1992) and transformants were selected for leucine prototrophy. These transformants were grown on defined media plates (SD supplemented with methionine, adenine, histidine, tryptophan, and uracil) and then patched onto MSA YEPD plates with and without thymidine (TdR) to test for the presence of a functional TK. The cells in MSA media displayed the dumbbell shaped morphology characteristic of DNA synthesis arrest while those in the MSA media with thymidine showed no such morphology. Together these results conclusively demonstrate that the exogenously introduced TK is functional. HS4.13 (pJM81) when grown on MSA YEPD plates also showed rescue when supplemented with 400 µg/ml of TdR.

Data indicate that pJM81 has, in the case of C4.32 (pJM81)and H4.31 (pJM81), integrated into the genome. Both these strains are unable to revert to leucine auxotrophy after extended periods of growth (30 generations) in non-selective conditions. In both strains, repeated screening using replica plating techniques have been unable to identify a single colony displaying leucine auxotrophy. Additionally, 0.5–1 µg of total DNA isolated from both these strains when transformed into E. coli by electroporation, do not result in any ampicillin resistant colonies. A control transformation performed using the same amount of total DNA from K2300 (pJM81) resulted in approximately 100 ampicillin resistant colonies. Together these results are convincing proof of the integration of pJM81 into the genomes of C4.32 and H4.31.

Introduction of a human TK gene into S. cerevisiae

A plasmid containing the human TK gene was made by excising the human TK gene from pMGK28 (Table 2) and inserting it into pVT103-U (Table 2) using the XhoI-HindIII sites. After confirmation by restriction mapping, the construct, now designated pLD4 (FIG. 7) was used to transform S. cerevisiae strains K2300, C4.32, H4.31 and HS4.13 by the one-step method (Chen et al., 1992). Transformants were selected using the vector encoded uracil marker. These four strains with the human TK were checked for TK function as in the case of the pJM81 containing strains.

All the above results confirm the construction of the strains required for the S. cerevisiae based system for testing potential dUTPase inhibitors. Thus the completed system consists of K2300, C4.32, H4.31 and HS4.13 with and without pJM81. The four strains without pJM81 can be used to test for inhibition by nucleoside analogues which is not dependent on the conversion of the nucleosidic form to the nucleosidic form, while the strains with pJM81 can be used to determine if these same analogues have the potential to inhibit dUTPase in the nucleosidic form.

II Effect of nucleoside derivatives (analogues) on growth of S. cerevisiae strains with the heterologous DUT genes The effects of a few nucleoside analogues on the growth of K2300, C4.32, H4.31 and HS4.13 strains with and without pJM81 were studied in an effort to determine if the S. cerevisiae system for testing dUTPase inhibitors functioned as intended. The analogues chosen for this purpose were 5-mercuri-2'-deoxyuridine (HgdUrd), and three other nucleoside analogues supplied by Oncorpharm Ltd. (Gaithersburg, Md. USA).

i) 5-Mercuri-2'-deoxyuridine (HgdUrd)

The growth of all four strains (K2300, C4.32, H4.31 and HS4.13) with and without pJM81 in the presence of HgdUrd was studied. Growth curves of these strains in 5 ml of defined media (SD with adenine, histidine, methionine, uracil and tryptophan), with HgdUrd at a final concentration of 5 µg/ml, when compared to the same strains' growth in defined media without HgdUrd, showed inhibition in all cases. This suggests that the presence or absence of pJM81 has no discernible effect on inhibition by HgdUrd. Thus inhibition of the S. cerevisiae strains was not limited to those possessing the TK construct (pJM81). Additionally, although an earlier study has demonstrated that HgdUrd did not inhibit C. albicans dUTPase in vitro (McIntosh et al., 1994), inhibition by HgdUrd was seen in both C. albicans DUTcontaining strains (C4.32 and C4.32 (pJM81)). These results suggest that the inhibition of the S. cerevisiae strains by HgdUrd resulted from the compound being non-specifically toxic and not from the inhibition of dUTPase itself. On examination by phase contrast microscopy cells from all strains were arrested at all stages of the cell cycle, as was evident by their morphology. This further supports the notion of the general toxicity of HgdUrd for S. cerevisiae.

ii) Other uridine analogues

Three compounds were assayed for their effect on K2300, C4.32 and H4.31 strains with and without pJM81. These three compounds were chosen on the basis of their structure as well as the structure of human dUTPase. The three compounds chosen were, 3'-azido-2'-deoxyuridine, 2'-Fluoro-2'-deoxyarabinose-Uracil (F-ara-U) and 2'-deoxy-pseudo-U (see Appendix D for structures). Given the specific interactions of dUTPase with the various key atoms of dUTP, the three compounds chosen all lacked a hydroxyl group at the 2' C and did not have bulky substituents at the C5 position of the base, both of which may cause steric hindrance and prevent interaction with dUTPase. They also possessed a hydrogen atom at the N3 position of the base which permitted hydrogen bonding to occur, thus satisfying the basic requisites for interaction with dUTPase.

Figure 8A:
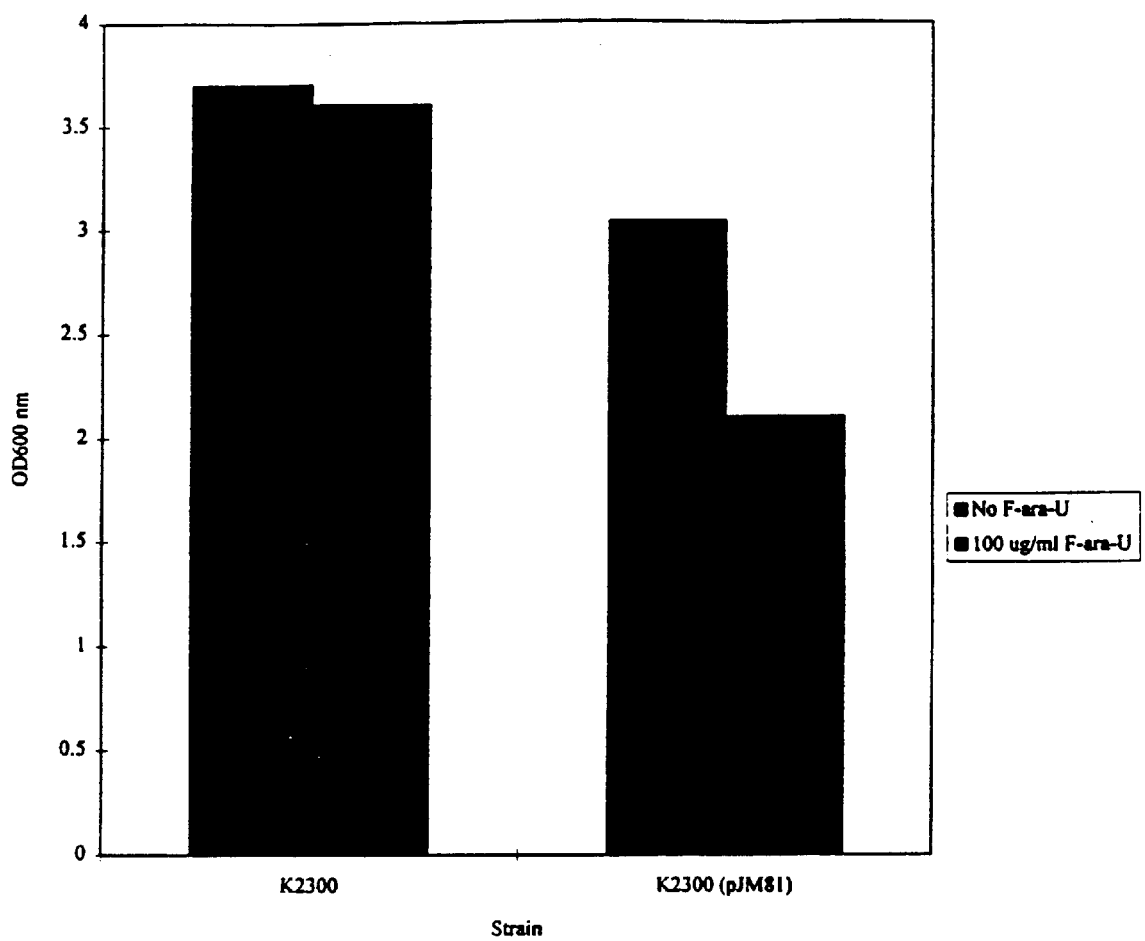
FIG. 8: Growth of *S. cerevisiae* strains in the presence of F-ara-U.
Figure 8B:
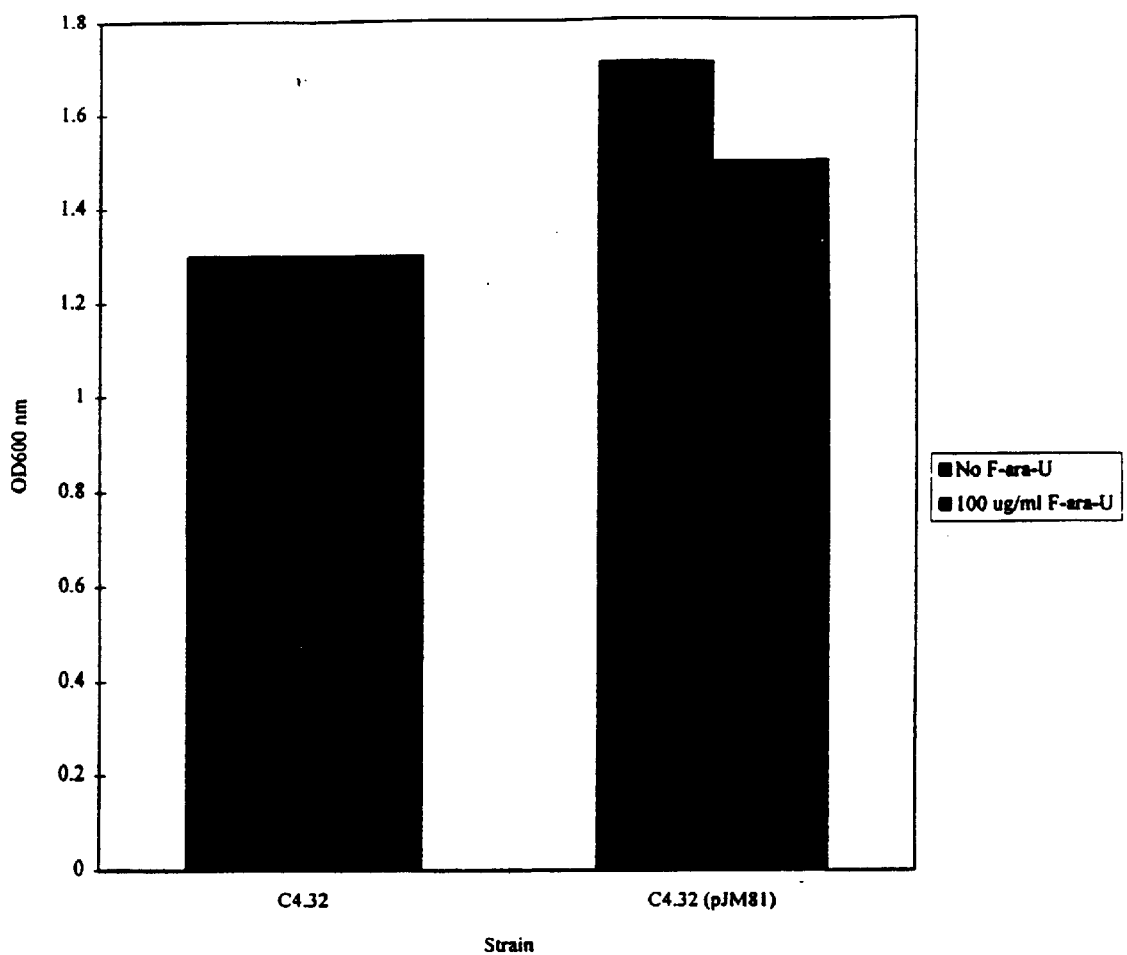
Figure 8C:
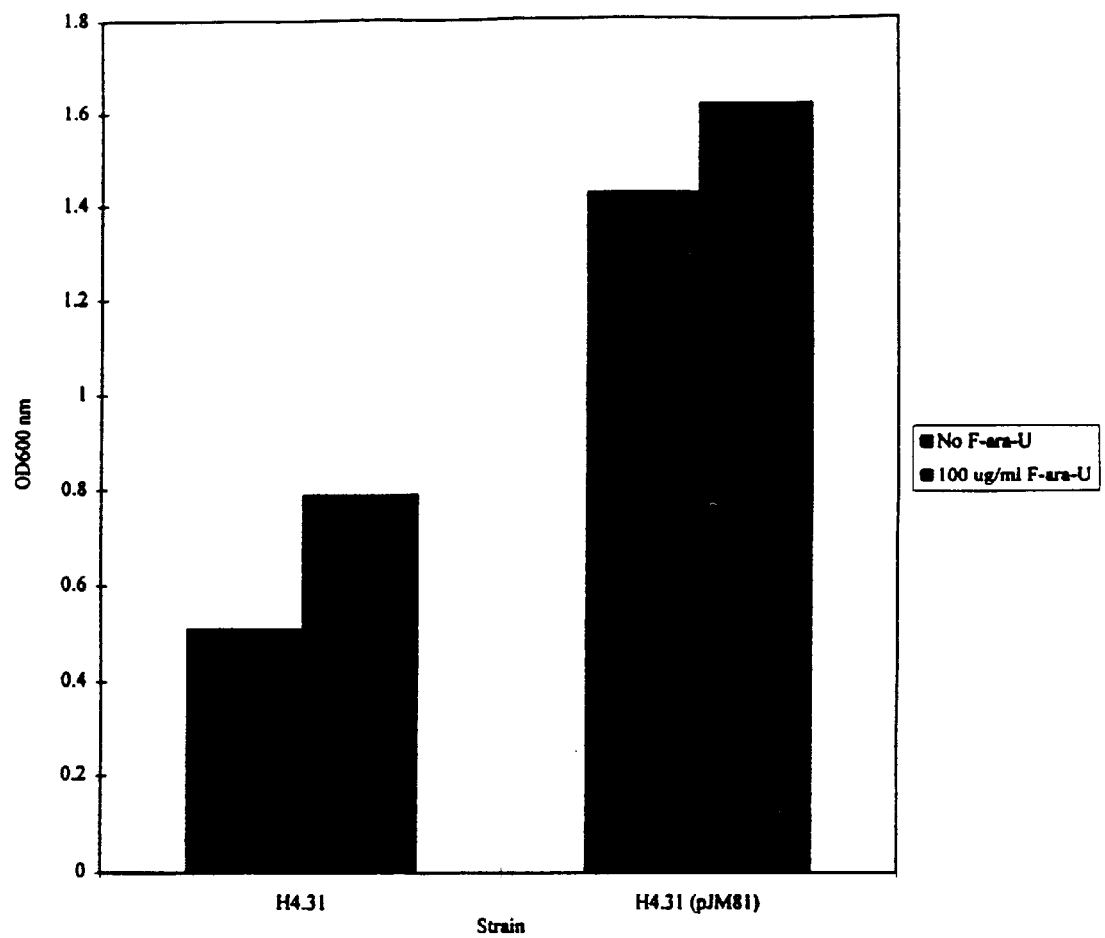

The primary screen consisted of assaying for the ability of these compounds to inhibit the growth of K2300, C4.32 and H4.31 all with and without pJM81. The assay was carried out in defined media in 13mm×100 mm test tubes in a final volume of 0.5 ml and at a final concentration of inhibitor of 100 µg/ml in each case. Visual inspection of the densities of the overnight cultures indicated that one of these three analogues, namely F-ara-U, may possess the ability to inhibit growth of K2300 (pJM81) and C4.32 (pJM81) but not K2300 and C4.32 (the same two strains without pJM81). Interestingly, H4.31 (pJM81) was not inhibited. A subsequent assay using 100 µg/ml F-ara-U in defined media, on K2300, C4.32 and H4.31 all with and without pJM81 was performed. Inhibition in the growth of K2300 (pJM81) and C4.32 (pJM81) was demonstrated (FIG. 8). F-ara-U (100 µg/ml) does not inhibit the growth of C4.32 (pJM81) grown in medium containing galactose. The morphology of C4.32 (pJM81) cells in the presence of F-ara-U was dumbbell shaped which is characteristic of DNA synthesis inhibition. Thus inhibition of these two S. cerevisiae strains by F-ara-U is related specifically to DNA synthesis, is dependent on conversion to the nucleosidic form, and is alleviated in C4.32 (pJM81) by growth in galactose containing medium. The lack of inhibition of H4.31 (pJM81) suggests that this inhibition is dUTPase specific.

LEGENDS FOR FIGS. 1–8

FIG. 1: The thymidylate synthesis pathway. Enzymes catalyzing the various reactions are: 1 ribonucleotide reductase; 2 nucleoside diphospate kinase; 3 dUTPase; 4 dCMP deaminase; 5 thymidylate synthetase (TS); 6 thymidylate kinase; 7 dihydrofolate reductase; 8 serine transhydroxymethylase; 9 thymidine kinase (TK); 10 deozynucleoside kinase; and 11 thymidine phosphorylase. Defines yeast genes such as DUT1, TMP1, CDC8 and DFR1 are also shown.

Figure 2:
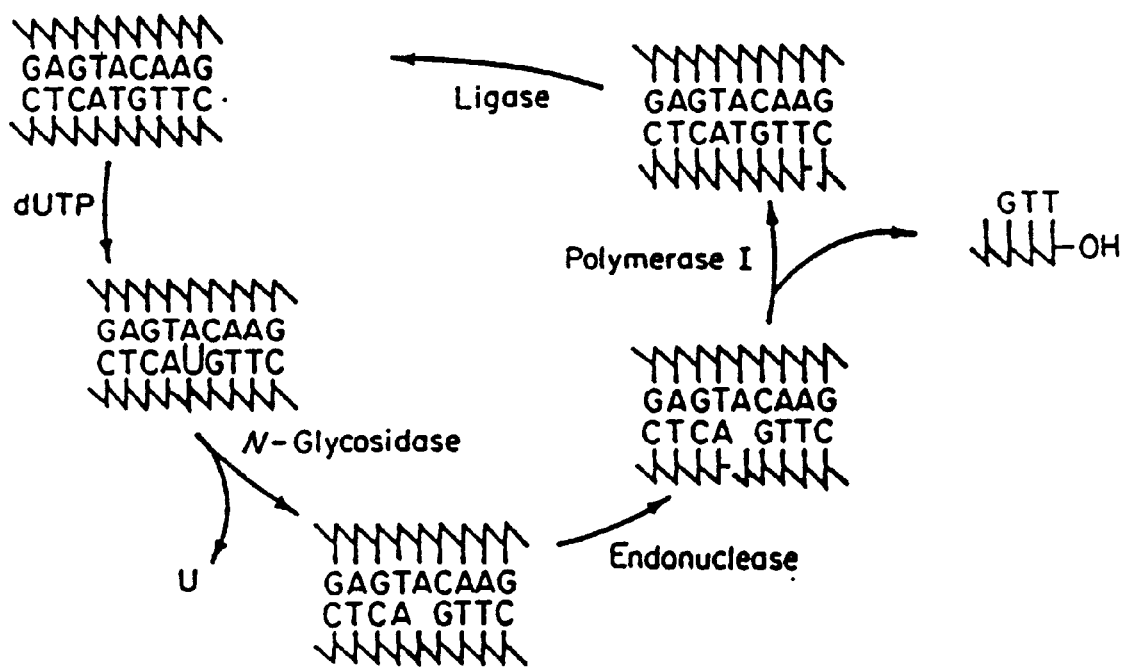
FIG. 2: Uracil excision repair.

FIG. 2: Uracil excision repair. (From Tye and Lehman 1987)

Figure 3:
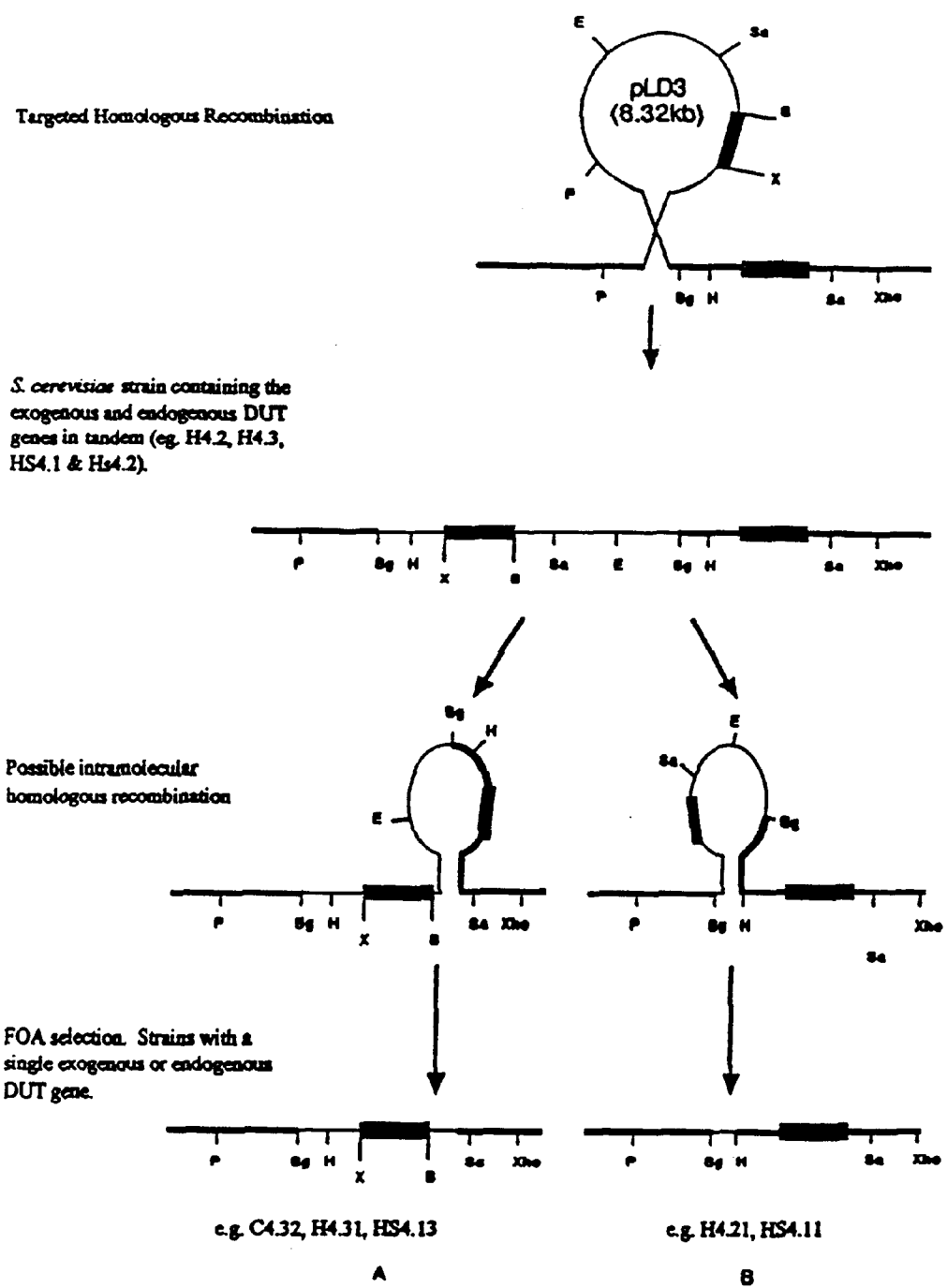
FIG. 3: Replacement of the *S. cerevisiae* DUT by an exogenous DUT.
Figure 4:
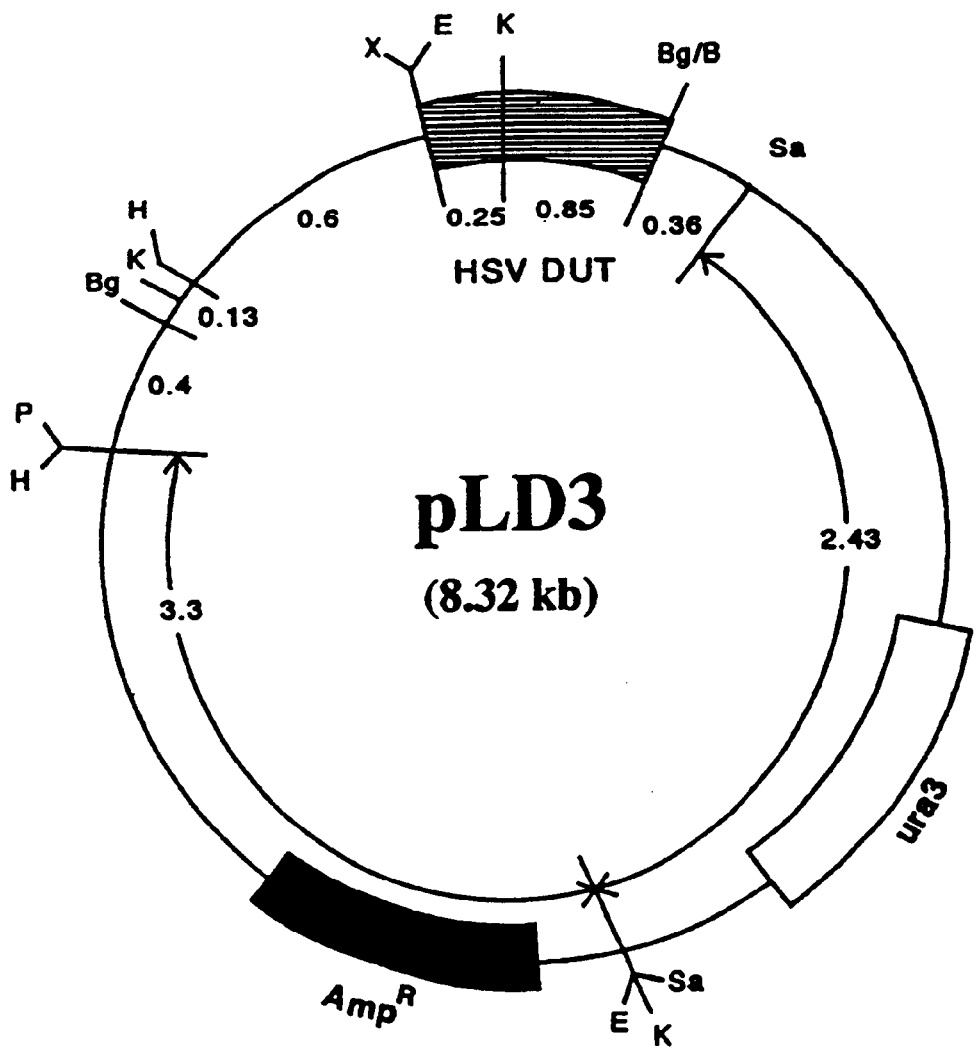
FIG. 4: Restriction map of pLD3.

FIG. 3: Replacement of the S. cerevisiae DUT by an exogenous DUT. Thick line represents S. cerevisiae genomic DNA, thin line represents plasmid introduced DNA, grey boxes denote endogenous DUT gene, black boxes denote either HSV or human DUT genes. (A) and (B) are URA3 deficient clones selected for by growing on FOA plates. Subsequent screening by Southern analysis and PCR analysis show (A) have retained exogenous DUT (eg. C4.32, H4.31 and HS4.13) while (B) have retained endogenous DUT (eg H4.21 and HS4.11).

FIG. 4: Restriction map of pLD3. HSV inserted at XbaI-BamHI of pLD7 using PCR primer encoded XbaI and BglII sites (Bg/B: BglII/BamHI ligation).

FIG. 5: Southern blot analysis of S. cerevisiae strains constructed. Lanes are designated according to the source of the genomic DNA, 1: Marker (λ DNA digested with HindIII and BglII); 2: K2300; 3: C4.32; 4: H4.31; 5: HS4.13; 6: K2300 (pJM81); 7: C4.32 (pJM81); 8: H4.31 (pJM81); 9: HS4.13 (pJM81); 10: K2300 (pLD4); 11: C4.32 (pLD4); 12: H4.31 (pLD4); 13: HS4.13 (pLD4). Arrows denote 1 Kb and 1.2 Kb fragments. (pJM81 and pLD4 are plasmids containing TK, construction of strains containing these plasmids is described on pages 61 and 72 respectively).

FIG. 6: PCR analysis of S. cerevisiae strains constructed. Lanes are designated according to the source of genomic DNA used as template. Lane 1: C4.32; 2: C4.32 (pJM81); 3: C4.32 (pLD4); 4: H4.31; 5: H4.31 (pJM81); 6: H4.31 (pLD4); 7: Marker (λ digested with BglII and HindIII); 8: HS4.13; 9: HS4.13 (pJM81); 10: HS4.13 (pLD4); Arrows indicate the PCR products, 0.475 Kb from the C4.32 strains; 0.450 Kb from the H4.31 strains and 1.2Kb from the HS4.13 strains.

Figure 7:
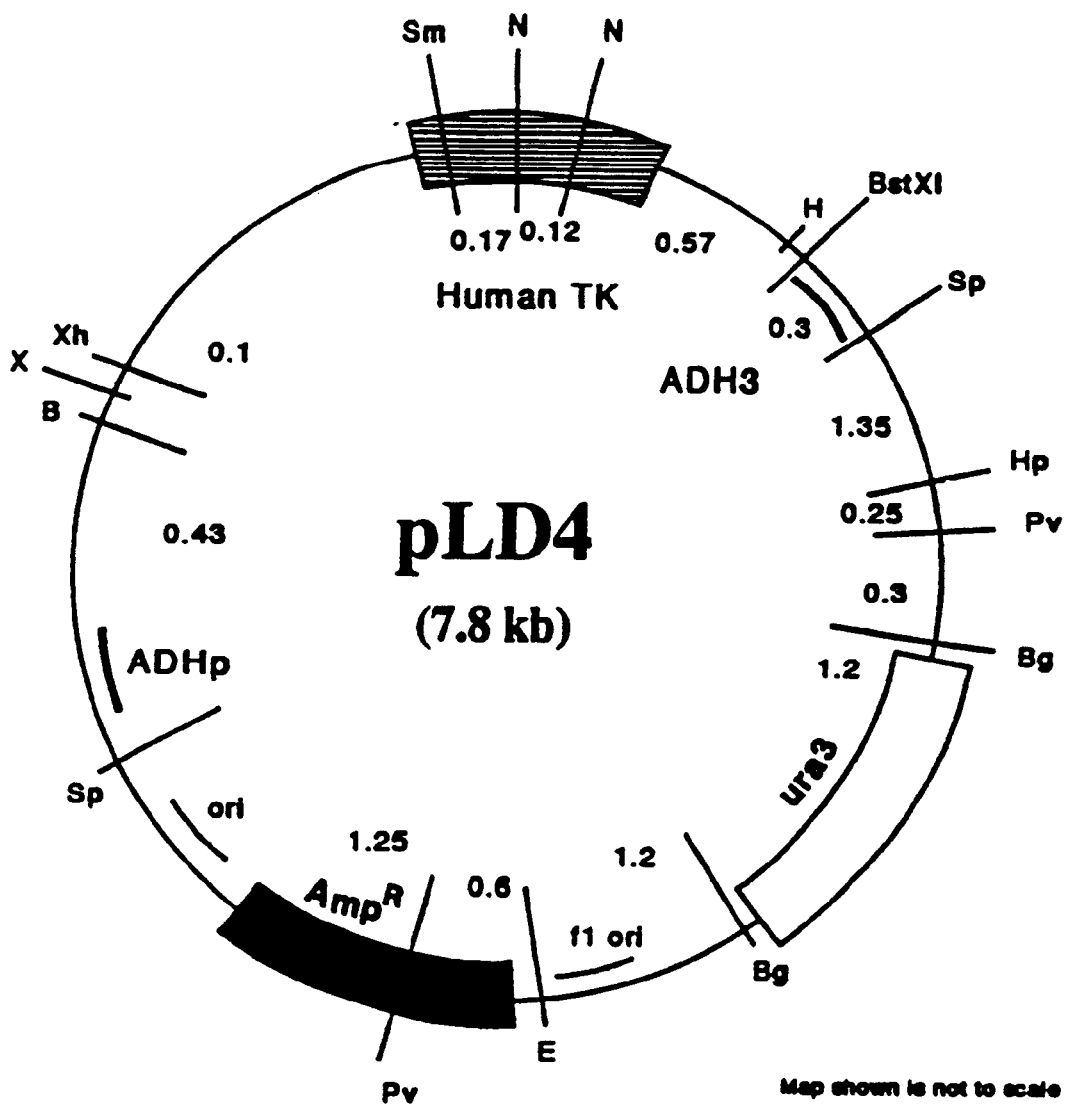
FIG. 7: Restriction map of pLD4.

FIG. 7: Restriction map of pLD4. Restriction site abbreviations are as indicated in earlier figures. N: NcoI; Pv: PvuI; Hp: HpaI; Sp: SphI; Sm: SmaI.

FIG. 8 (A-C): Growth of S. cerevisiae in the presence of F-ara-U. Growth of K2300, C4.32, and H4.31 with and without pJM81 in the presence and absence of F-ara-U (100 µg/ml).(A) K2300 strains, (B) C4.32 strains and (C) H4.31 strains.

REFERENCES

Bergstrom D. E. and Ruth J. L. (1977). Preparation of C-5 mercurated pyrimidine nucleosides. *J Carbohydrates. Nucleosides. Nucleotides.*; 4, 257–269.

Chen D., Yang B. and Kno T. (1992). One-step transformation of yeast in stationary phase. *Curr. Genet.*, 21, 83–84.

DeSouza L. (1995). Replacement of the genomic Saccharomyces cerevisaie DUT gene by a Candida albicans DUT gene and insertion of the Candida albicansDUTgene into an expression vector. Honours Thesis York University.

Fienberg A. P. and Vogelstein B. (1983). A technique for radiolabelling DNA restriction endonuclease fragments to high specific activity. *Analytical Biochem.*, 132, 6–13.

Grivell A. R. and Jackson J. F. (1968). Thymidine kinase: Evidence for its absence from *Neurospora crassa*, and some other microorganisms, and the relevance of this to the specific labelling of deoxyribonucleic acid. *J Gen. Microbiol.*, 54, 307–317.

Heery D. M., Gannon F. and Powell R. (1990). A simple method for subcloning DNA fragments from gel slice. *Trends in Genet.*, 6, 137.

Hogan J. C. (Jr) (1996). Directed combinatorial chemistry. *Nature*, 384 (supp). 17–19.

Holliday J. and Williams M. V. (1991). Inhibition of herpes simplex virus types 1 and 2 replication in vitro by mercurithio analogues of deoxyuridine. *Antivir. Res.*, 16, 197–203.

Köhrer K. and Domdey H. (1991). "Preparation of high molecular weight RNA." in Guide to yeast genetics and molecular biology. Eds. Guthrie C. and Fink G. R. *Methods in Enzymology*, 194, 398–405.

Little J. G. and Haynes R. H (1979). Isolation and characterization of yeast mutants auxotrophic for 2'-deoxythymidine 5'-monophosphate. *MoL Gen. Genet.*, 168, 141–151.

McIntosh E. M., Kunz B. A. and Haynes R. H. (1986b). Inhibition of DNA replication in *Saccharomyces cerevisiae* by araCMP. *Curr. Genet.*, 10, 579–585.

McIntosh E. M., Looser, J., Haynes, R. H., and Pearlman, R. E. (1994) MluI site-dependent transcriptional regulation of the *Candida albicans* dUTPase gene. *Curr. Genet.*, 26, 415–421.

McNeil J. B. and Friesen J. D. (1981) Expression of the Herpes Simplex Virus Thymidine Kinase gene in *Saccharomyces cerevisiae*. *Mol. Gen. Genet.*, 184, 386–393.

McNeil J. B. and Little J. G. (1985). Yeast/Herpes Simplex Virus thymidine kinase gene fusions yield fusion proteins with thymidine kinase activity. *Curr. Genet.*, 9, 567–572.

Sambrook J., Fritsch E. F. and Maniatis T. (1989) Molecular Cloning: A laboratory manual, Cold Spring Harbour Laboratory.

Sherman F. (1991). "Getting started with yeast." in Guide to yeast genetics and molecular biology. Eds. Guthrie C. And Fink G. R. *Methods in Enzymology*, 194, 3–21.

Sikorski R. S. and Boeke J. D. (1991) "In vitro mutagenesis and plasmid shuffling: From cloned gene to mutant yeast." in Guide to yeast genetics and molecular biology. Eds. Guthrie C. and Fink G. R. *Methods in Enzymology*, 194, 302–318.

Tye B-K. and Lehman I. R. (1977). Excision repair of uracil incorporated in DNA as a result of a defect in dUTPase. *J Mol. Biol.*, 117, 293–306.

Vernet T., Dignard D. and Thomas, D. Y. (1987). A family of yeast expression vectors containing the phage f1 intergenic region. *Gene* 52, 225–233.

TABLE 1

Bacterial and Yeast Strains

| Strain | Description/ Genotype | Source |
|---|---|---|
| *E. Coli* strain | | |
| DH5α F' | F', supE44, Δlac U169(Φ 80, lacZ ΔM15), hsdR17, recA1, end A1, gyrA96, thi-1, relA1. | — |
| *S. cerevisiae* strains | | |
| K2300 | MAT a, ho - LacZ, ura-3, ade2-1, met, his3, leu2, trp1, can1-100 | E. McIntosh |

TABLE 1-continued

Bacterial and Yeast Strains

| Strain | Description/ Genotype | Source |
|---|---|---|
| C4.32 and C4.41 | Isogenic with K2300, but with DUT1 replaced by the *C. albicans* DUT. | L. DeSouza (1995) |
| H4.2 and H4.3 | K2300 with human DUT and URA3 inserted adjacent to the endogenous DUT1. (FIG. 7) | L. DeSouza (1995) |
| H4.31 and H4.32 | H4.3 with the endogenous DUT1 and URA3 excised. (FIG. 7) | This Example |
| H4.21 | H4.2 with the human DUT and URA3 excised. (FIG. 7) | This Example |
| HS4.1 and HS4.2 | K2300 with HSV DUT and URA3 inserted adjacent to the endogenous DUT1. (FIG. 7) | This Example |
| HS4.13, HS4.16 and HS4.111 | HS 4.1 with the endogenous DUT1 and URA3 excised. (FIG. 7A) | This Example |
| HS4.11 | HS4.1 with the HSV DUT and URA3 genes excised. (FIG. 7B) | This Example |

TABLE 2

Plasmids

| Plasmid | Description | Source/Reference |
|---|---|---|
| p22.22 (FIG. 4) | pBS (Stratagene) + Pst I - Bam HI insert containing the *S.cerevisiae* DUT1 with a GAL1 UAS element 5' to it. (Bam HI site was then deleted.) | L. Desouza (1995) |
| pLD7 (FIG. 5) | p22.22 without the *S. cerevisiae* DUT1 coding region, with 1.83 Kb insert containing URA3 at the XhoI site. | L. DeSouza (1995) |
| pLD3 (FIG. 8) | pLD7 with HSV DUT at the XbaI - BamHI site. | This Example |
| pMGK28 (FIG. 6) | Human TK cDNA in pBluescript II KS (Stratagene) inserted at the XhoI - ClaI site. | T. Kelly, Johns Hopkins University. |
| pVT103-U | Yeast expression vector | Vernet et al. (1987) |
| pLD4 | pVT103-U with the Human TK from pMGK28 at the XbaI - BamHI site. | This Example |
| pJM81 | HSV TK containing construct. | McNeil and Freisen (1981) |
| p1313 | YEP13 with *S. cerevisiae* DUT inserted at the HindIII - BamHI sites. | J. McNeil |
| HELIR1RV | plasmid containing HSV DUT cDNA | R. L. Thompson Univ. of Cincinnati Medical Center. |

TABLE 3

Primers

| Primer | Sequence | Restriction site included |
|---|---|---|
| CAX | 5'-GGAATCTAGAATGACTTCAGAAGACCAA-3' | XbaI |
| CAB | 5'-GGTTGGATCCTAGTTCTTACCAGTAGA-3' | BamHI |
| HUX | 5'-GGAATCTAGAATGCAGCTCCGCTTTGCC-3' | XbaI |
| HUB | 5'-GGTTGGATCCTTAATTCTTTCCAGTGGA-3' | BamHI |
| HSX | 5'-GGCTCTAGAATTCATGAGTCAGTGGGG-3' | XbaI and |

TABLE 3-continued

Primers

| Primer | Sequence | Restriction site included |
|---|---|---|
| HSB | 5'-GCGAGATCTCTAAATACCGGTAGAACC-3' | EcoRI BglII |
| CDUTHIS | 5'-ACCTTGGCATATGCATCACCATCACCATCA CACTTCAGAAGACCAATCCCTTAAG-3' | NdeI |
| CDUT | 5'-CCTTGGAATTCTTACTAGTTCTTACCAGTAG ATCCAAAA-3' | EcoRI |
| cDUT5 | 5'-GACTACTTTCACTTCACC-3' | — |
| cDUT6 | 5'-CATAGCCAGCAGCAAGTG-3' | — |

TABLE 4

Media

| Media (per liter) | Constituents |
|---|---|
| | For *E. Coli* |
| YT | 10 g Bacto-tryptone, 5 g yeast extract, 5 g NaCl, (For plates add 15 g agar). |
| SOC medium | 20 g Bacto-tryptone, 5 g Bacto-yeast extract, 0.5 g NaCl, 10 ml 250 mM KCl, 5 ml 2M $MgCl_2$, 20 ml 1M glucose. |
| | For *S. cerevisiae* |
| SD | 6.7 g yeast nitrogen base without amino acids plus $(NH_4)_2SO_4$, 20 g glucose. (For plates add 20 g agar). |
| YEPD | 10 g yeast extract, 20 g Bacto-peptone, 20 g glucose. (For plates add 20 g agar). |
| YEPG | Same as YEPD but with 20 g galactose instead of glucose. |
| MSA YEPD/ MSA | Same as YEPD/ YEPG but with 5 mg/ml sulfanilamide, |
| YEPG | 100 µg/ml amethopterin (Sigma) 1.5 mg/ml $KH_2PO_4$ |
| FOA plates | 7 g yeast nitrogen base without amino acids plus $(NH_4)_2SO_4$, 375 ml $dH_2O$, 100 ml 20% glucose, 500 ml 4% agar 25 ml (2 mg/ml) uracil. 1 g 5-fluoro orotic acid added after autoclaving and cooling to 55° C. |

TABLE 5

Buffers and Solutions

| Buffer/ Solution | Constituents |
|---|---|
| TE | 10 mM TrisHCl (pH 7.4), 1 mM EDTA |
| TEB (Electrophoresis buffer, 1 L) | 10 g Tris base, 5.5 g Boric acid, 0.93 g EDTA pH adjusted to 8.0 |
| Gel loading solution (6X) | 0.25% Bromophenol blue, 0.25% Xylene cyanol F.F., 40% (w/v) sucrose in water. |
| SSPE (20x, 1L) | 175.3 g NaCl, 27.6 g $NaH_2PO_4$, 7.4 g EDTA, pH adjusted with NaOH (pH 7.4). |
| SSC (20x, 1L) | 175.3 g NaCl, 88.2 g Sodium citrate, pH adjusted with NaOH (pH 7.0). |
| STE | TE at pH 8.0 containing 0.1 M NaCl. |
| Sodium Acetate buffer | 50 mM Sodium Acetate, 10 mM EDTA, pH adjusted with acetic acid (pH 5.0). |
| Chloropane | 50% liquified phenol, 50% chloroform, 0.5% 8-hydroxyquinoline. |

C) Effect of F-ara-U on H4.3 1 strains.

| | $OH_{600\,nm}$ | | | | | |
|---|---|---|---|---|---|---|
| Strain | 0 hrs | 4 hrs | 8 hrs | 12 hrs | 22 hrs | 26 hrs |
| | Defined media only | | | | | |
| H4.31 | 0.08 | 0.095 | 0.18 | 0.51 | 5.2 | 5.6 |
| H4.31 (pJM81) | 0.065 | 0.116 | 0.29 | 1.43 | 8.0 | 8.4 |
| | Defined media with F-ara-U (100 µg/ml) | | | | | |
| H4.31 | 0.067 | 0.093 | 0.21 | 0.79 | 5.5 | 5.3 |
| H4.31 (pJM81) | 0.072 | 0.13 | 0.41 | 1.62 | 7.7 | 9.0 |

NB. All data above were generated using a single culture of each strain in each medium. Overnight cultures were grown in the defined media without F-ara-U and then inoculated into defined media with and without F-ara-U. These resultant cultures were then used to generate the above data.

Structures of uridine analogues used.

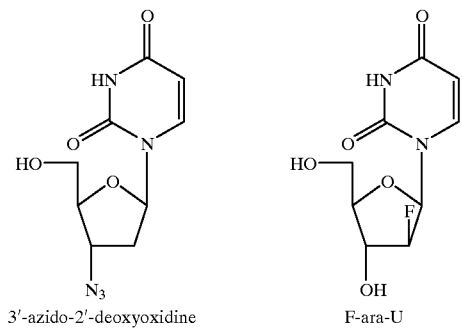

3'-azido-2'-deoxyoxidine     F-ara-U

-continued

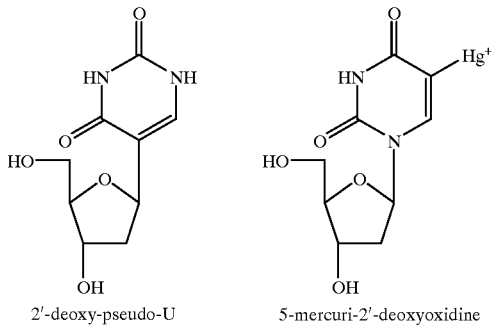

2'-deoxy-pseudo-U         5-mercuri-2'-deoxyoxidine

We claim:

1. A method of identifying an agent useful to impair the growth of a target organism or cell, the method comprising the steps of:
   obtaining a viable yeast strain in which the endogenous DUT gene has been replaced and functionally complemented by a heterologous DUT gene from said target organism or cell, said yeast strain being dependent for growth on the activity of dUTPase expressed from said heterologous DUT gene,
   incubating said yeast strain with a candidate inhibitor of said dUTPase expressed from said heterologous DUT gene, and
   determining the effect of the candidate inhibitor on the activity of said dUTPase by assessing the rate and morphology of growth of said yeast strain, whereby agents that impair the growth of said target organism or cell are identified as those candidate inhibitors of dUTPase that impair the growth rate and induce a DNA synthesis arrest morphology of said yeast strain when incubated therewith.

2. A method in accordance with claim 1, wherein the target organism comprises a human cell.

3. A method in accordance with claim 1, wherein the target organism comprises a pathogen.

4. A method in accordance with claim 3, wherein the target pathogen is selected from the group comprising viruses, bacteria, fungi and protozoa.

5. A method in accordance with claim 3, wherein the target pathogen is selected from the group consisting of herpes simplex virus, *C. albicans, Plasmodium falciparum* and *Aspergillus fumigatus*.

6. A method in accordance with claim 3, wherein the target pathogen is herpes simplex virus.

7. A method in accordance with claim 3, wherein the target pathogen is *C. albicans*.

8. A method in accordance with claim 1, wherein the yeast strain comprises *S. cerevisiae*.

9. A method in accordance with claim 1, wherein the yeast strain further comprises a cloned thymidine kinase encoding gene.

10. A method in accordance with claim 9, wherein the thymidine kinase encoding gene is HSV thymidine kinase encoding gene.

11. A method in accordance with claim 9, wherein the thymidine kinase encoding gene is human thymidine kinase encoding gene.

12. A method according to claim 1 for use in assaying for dUTPase inhibitors of herpes simplex virus (HSV), wherein said yeast strain comprises *S. cerevisiae* in which the endogenous dUTPase encoding gene has been replaced with the dUTPase encoding gene from HSV.

13. A method in accordance with claim 12, wherein the *S. cerevisiae* further comprises a cloned thymidine kinase encoding gene.

14. A method according to claim 1 for use in assaying for dUTPase inhibitors of *C. albicans*, wherein said yeast strain comprises *S. cerevisiae* in which the endogenous dUTPase encoding gene has been replaced with the dUTPase encoding gene from *C. albicans*.

15. A method in accordance with claim 14, wherein the *S. cerevisiae* further comprises a cloned thymidine kinase encoding gene.

16. A method according to claim 1 for use in assaying for dUTPase inhibitors of human cells, wherein said yeast strain comprises *S. cerevisiae* in which the endogenous dUTPase encoding gene has been replaced with the dUTPase encoding gene from human cells.

17. A method in accordance with claim 16, wherein the *S. cerevisiae* further comprises a cloned thymidine kinase encoding gene.

18. A method according to claim 9, wherein the candidate inhibitor is a nucleosidic inhibitor.

19. The method according to claim 1, comprising the further steps of comparing said rate and morphology of growth of said viable yeast strain with that of a control yeast strain in which the endogenous DUT gene has been replaced and functionally complemented by a heterologous DUT gene from a human cell, and selecting an agent that impairs the growth rate and morphology to an extent that is greater for said viable yeast strain than for said control yeast strain.

20. A viable strain of *S. cerevisiae* in which the endogenous dUTPase encoding gene has been replaced with the dUTPase encoding gene from HSV.

21. A viable strain of *S. cerevisiae* in which the endogenous dUTPase encoding gene has been replaced with the dUTPase encoding gene from HSV and which further comprises a cloned thymidine kinase encoding gene.

22. A viable strain of *S. cerevisiae* in which the endogenous dUTPase encoding gene has been replaced with the dUTPase encoding gene from *C. albicans*, deposited at ATCC under accession no. 74421.

23. A viable strain of *S. cerevisiae* in which the endogenous dUTPase encoding gene has been replaced with the dUTPase encoding gene from *C. albicans* and which further comprises a cloned thymidine kinase encoding gene from HSV, deposited at ATCC under accession no 74423.

24. A viable strain of *S. cerevisiae* in which the endogenous dUTPase encoding gene has been replaced with the dUTPase encoding gene from human cells, deposited at ATCC under accession no. 74420.

25. A viable strain of *S. cerevisiae* in which the endogenous dUTPase encoding gene has been replaced with the dUTPase encoding gene from human cells and which further comprises a cloned thymidine kinase encoding gene from HSV, deposited at ATCC under accession no 74422.

* * * * *